United States Patent
Conrad et al.

[11] Patent Number: 5,965,712
[45] Date of Patent: Oct. 12, 1999

[54] LZ-CD23 CHIMERA FOR INHIBITION OF IGE-MEDIATED ALLERGIC DISEASE

[75] Inventors: Daniel H. Conrad, Middletown; Ann E. Kelly, Annandale, both of Va.

[73] Assignee: Virginia Commonwealth University, Richmond, Va.

[21] Appl. No.: 09/100,398

[22] Filed: Jun. 19, 1998

[51] Int. Cl.[6] .................................................. C07K 14/735
[52] U.S. Cl. ........................................................... 530/396
[58] Field of Search ............................................. 530/396

[56] References Cited

U.S. PATENT DOCUMENTS 5,554,523   9/1996   Reddy ..................................... 435/194

OTHER PUBLICATIONS

Beavil, A.J., Alpha–helical coiled–coil stalks in the low–affinity receptor for IgE (FcepsilonRII/CD23) and related C–type lectins. Proc. Natl. Acad. Sci. USA. 89:753–757, Jan. 1992.

Klein, N.J. Il–4 regulates the morphology, cytoskeleton, and proliferation of human umbilical vein endothelial cells: relationship between vimentin and CD23. Internatl. Immunol. 5(3):293–301, 1993.

Sakuma, H., et al., Molecular cloning and functional expression of a cDNA encoding a new member of mixed lineage kinase from human brain. Jour. Biol. Chem. 272(45):28622–28629, Nov. 1997.

*Primary Examiner*—David Saunders
*Assistant Examiner*—Mary Beth Tung
*Attorney, Agent, or Firm*—Whitham Curtis & Whitham

[57] ABSTRACT

CD23 is a low affinity receptor for IgE. The extracellular part of this molecule has been linked to a modified leucine zipper. This results in a trimeric configuration, since the stalk region of the CD23 molecule is itself a weak leucine zipper. This chimeric protein, designated LZ-CD23, interacts with IgE in a much stronger fashion than either simply the extracellular domain alone or the intact membrane CD23. This is the result of an increased avidity due to the stable trimeric configuration. The chimera has approximately at 10,000 fold increased ability to block IgE binding to mast cell/basophils, compared to native soluble CD23. At approximately equal concentrations to added IgE, 80% inhibition of IgE binding to FcЄRI on mast cells was obtained. Thus, the LZ-CD23 chimera provides a new means for blocking and binding which provides benefits in the treatment of IgE-mediated asthma and allergic diseases.

1 Claim, 7 Drawing Sheets

SEQUENCE LISTING

```
<160> NUMBER OF SEQ ID NOS: 17

<210> SEQ ID NO 1
<211> LENGTH: 23
<212> TYPE: DNA
<213> ORGANISM: primer

<400> SEQUENCE: 1
caycgaagct tgtgaggacc atg                                           23

<210> SEQ ID NO 2
<211> LENGTH: 20
<212> TYPE: DNA
<213> ORGANISM: primer

<400> SEQUENCE: 2
cttctttcaa cattttcact                                               20

<210> SEQ ID NO 3
<211> LENGTH: 24
<212> TYPE: DNA
<213> ORGANISM: primer

<400> SEQUENCE: 3
gatcccggga tttcaaaggg aact                                          24

<210> SEQ ID NO 4
<211> LENGTH: 24
<212> TYPE: DNA
<213> ORGANISM: primer

<400> SEQUENCE: 4
acaaagatcc tctagagtcg cggc                                          24
```

-continued

```
<210> SEQ ID NO 5
<211> LENGTH: 22
<212> TYPE: DNA
<213> ORGANISM: primer

<400> SEQUENCE: 5
tcacacagga aacagctatg ac                                              22

<210> SEQ ID NO 6
<211> LENGTH: 27
<212> TYPE: DNA
<213> ORGANISM: primer

<400> SEQUENCE: 6
aatgttaacg gaggacaagc gcctcag                                         27

<210> SEQ ID NO 7
<211> LENGTH: 21
<212> TYPE: DNA
<213> ORGANISM: primer

<400> SEQUENCE: 7
ggcgttaacg agaagcgcac a                                               21

<210> SEQ ID NO 8
<211> LENGTH: 26
<212> TYPE: DNA
<213> ORGANISM: primer

<400> SEQUENCE: 8
gaatagtcga ctctagatgc atgctc                                          26

<210> SEQ ID NO 9
<211> LENGTH: 24
<212> TYPE: DNA
<213> ORGANISM: primer

<400> SEQUENCE: 9
atcgatatgg aagaaaatga atac                                            24

<210> SEQ ID NO 10
<211> LENGTH: 21
<212> TYPE: DNA
<213> ORGANISM: primer

<400> SEQUENCE: 10
cttgcaaggc ttgtgacatc t                                               21

<210> SEQ ID NO 11
<211> LENGTH: 22
<212> TYPE: DNA
<213> ORGANISM: primer

<400> SEQUENCE: 11
gtcgactcag ggttcacttt tt                                              22

<210> SEQ ID NO 12
<211> LENGTH: 24
<212> TYPE: DNA
<213> ORGANISM: primer

<400> SEQUENCE: 12
cgggatccat ggaagaaaat caat                                            24
```

```
<210> SEQ ID NO 13
<211> LENGTH: 25
<212> TYPE: DNA
<213> ORGANISM: primer

<400> SEQUENCE: 13
ggaattctca gggttcactt tttgg                                           25

<210> SEQ ID NO 14
<211> LENGTH: 23
<212> TYPE: DNA
<213> ORGANISM: primer

<400> SEQUENCE: 14
ctgctgaatt cttggcactg gga                                             23

<210> SEQ ID NO 15
<211> LENGTH: 24
<212> TYPE: DNA
<213> ORGANISM: primer

<400> SEQUENCE: 15
tgatggatat gcggccgctt ctca                                            24

<210> SEQ ID NO 16
<211> LENGTH: 30
<212> TYPE: DNA
<213> ORGANISM: primer

<400> SEQUENCE: 16
tacgactcaa tcgatggaga cccaagcttg                                      30

<210> SEQ ID NO 17
<211> LENGTH: 29
<212> TYPE: DNA
<213> ORGANISM: primer

<400> SEQUENCE: 17
aggttccttc acgtcgaccc tctagcatt                                       29
```

LZ-CD23 CHIMERA FOR INHIBITION OF IGE-MEDIATED ALLERGIC DISEASE

This invention was made using funds from grants from the United States Public Health Services, Grant No. AI 18697. The government may have certain rights in this invention.

DESCRIPTION

ABBREVIATIONS

The following abbreviations are used in this patent specification: Fc∈RII, the low affinity receptor for IgE; sCD23, soluble CD23; EC-CD23, soluble CD23 construct consisting of entire extracellular domain; MBP-CD23, soluble CD23 chimera consisting of the lectin head of CD23 attached to the leader sequence and stalk of Mannose Binding Protein; CD72-CD23, CD23 chimera consisting of the lectin head of CD23 and the cytoplasmic, transmembrane, and stalk domain of CD72; CD72-CD23 neck, CD23 chimera consisting of the same region of CD72 attached to the "neck" and lectin head domains of CD23; human-mouse CD23, CD23 chimera consisting of the lectin head of a murine CD23 attached to the cytoplasmic, transmembrane, and stalk domain of human CD23; C1M, cleavage mutant 1; lzEC-C1M, sCD23 chimera consisting of a modified isoleucine zipper attached to the amino terminus of the entire extracellular domain of C1M; COS, African green monkey kidney cells; CHO, Chinese hamster ovary cells; Fc∈RI, the high affinity receptor for IgE; and a.a., amino acid.

BACKGROUND OF THE INVENTION

Field of the Invention

The invention is directed to a compound and method for treatment of IgE-mediated disorders.

Background Description

The low affinity receptor for IgE, Fc∈RII$^4$ or CD23 (1), is a type II integral membrane protein expressed on murine B cells (2), and FDCs (3). Structurally CD23 consists of carboxyl terminal lectin head, a stalk consisting of four 21-amino acid repeat domains, and a transmembrane and cytoplasmic domain (4). Both human (5) and murine (6) CD23 has been found to exist as both a membrane and a soluble protein, the latter is a result of proteolytic cleavage. Through the use of CD23 transgenic (7;8) and knockout mice (9), this receptor has been implicated in the regulation of Ig production, specifically IgE.

In the past several years, two new ligands for CD23 have been identified. CD21, or CR2, is expressed on B cells and interactions between these two proteins may enhance homotypic aggregation {Bjorck, ElenstroMagnusson, et al. 1993 ID: 4259} between B cells. In addition, this interaction has been proposed to play a role in IgE regulation (10). More recently, human (11) and murine (12) CD23 have been shown to interact with CD11b/CD18 on monocytes and this interaction results in inflammatory cytokine release (11;12). The interaction with these other ligands, especially CD11b/CD18, has shown CD23s involvement in immunity through interactions with receptors on both lymphoid and non-lymphoid cells.

Previous work using several different chimeras (13;14) or a full-size recombinant form of CD23 (EC-CD23) (14) determined that the stalk of CD23 is important in mediating oligomerization of the protein allowing for a high affinity interaction with IgE via avidity considerations. While ED-CD23 has previously been shown to interact with IgE, albeit with a lower affinity than membrane CD23 was still desired. In this regard, several chimeras were made containing stalks that were not subject to proteolytic degradation to further ascertain which domains of CD23 are important in mediating the interaction with IgE. It was found that addition of a trimeric isoleucine zipper to the entire extracellular region of CD23 resulted in a soluble construct that bound IgE in a manner at least equivalent to membrane CD23.

Several groups are now examining antibodies for use in allergic disease. However, antibodies bind to Fc receptors and can have serious side effects.

SUMMARY OF THE INVENTION

It is an object of this invention to provide a new anti-IgE substance which can be used in a wide variety of clinical applications including blocking IgE binding to mast cells, treatment of IgE-mediated asthma and allergic diseases, and in gene therapy in the treatment of allergic diseases.

The low affinity receptor for IgE (Fc∈RII/CD23) interacts with IgE with a dual affinity. Three chimeric constructs were created containing the lectin domain (a.a. 172 through 188) or the "neck" and lectin domain (a.a. 157 through 188) attached to subunits of oligomeric proteins. All chimeras were incapable of interacting with IgE with a either a high or low affinity indicating that the -helical stalk of CD23 is important for orienting the lectin heads such that an interaction with IgE can occur. This concept received further support in that a chimeric CD23 composed of the human CD23 stalk and the mouse CD23 lectin head bound mouse IgE with a dual affinity, but could only bind rat IgE with a low affinity. Effort was concentrated on a construct consisting of the entire extracellular region of CD23 (EC-CD23). A mutation to the first cleavage site of CD23 (C1M) resulted in a more stable molecule as determined by a decrease of sCD23 release. A soluble chimeric EC-C1M was prepared by attaching an isoleucine zipper to the amino terminus (lzEC-1M). The interaction with IgE by lzEC-C1M was found to be superior to that seen with EC-CD23. The lzEC-C1M could inhibit binding of IgE to both CD23 and the high affinity receptor for IgE, Fc∈RI, providing further evidence for a strong interaction with IgE. Fc∈RI inhibition (ca. 80%) was seen at equimolar concentrations of lzEC-C1M implying the effectiveness of this chimera and its therapeutic value.

BRIEF DESCRIPTION OF THE DRAWINGS

The foregoing and other objects, aspects and advantages will be better understood from the following detailed description of the preferred embodiments of the invention with reference to the drawings, in which:

FIG. 7 is a schematic representation of lzEC-C1M. The lzEC-C1M contains a modified isoleucine zipper motif attached to the amino terinus of the entire extracellular domain of CD23. The lectin head of CD23 consists of a.a. 189 to the end, the putative "neck" domain consists of a.a. 157 to 188, and the stalk domain contains a.a. 55–157. Numbering refers to the original predicted a.a. sequence of murine CD23 discussed in Bettler et al., *Proc. Natl. Acad. Sci. USA* 85:1907 (1988).

DETAILED DESCRIPTION OF THE PREFERRED EMBODIMENTS OF THE INVENTION

A new chimera for inhibiting IgE-mediated allergic disease has been discovered. This new chimera blocks IgE binding to mast cells/basophils 10,000 fold better than native soluble CD23, and has comparable blocking and binding efficiency to antibodies which bind to Fc receptors but without the side effects. With the exception of isoleucine for leucine substitutions on the zipper portion of the molecule, it is entirely self in nature and an immunologic reaction to the chimera would not be expected to be generated. Thus, this new chimera is a significant improvement to current anti-IgE approaches.

MATERIALS AND METHODS

Cell Culture, Antibodies, and Immunosorbants

African green monkey kidney cells (COS) were obtained from ATCC (Bethesda, Md.) and used for transient expression of chimeric proteins. COS were maintained in supplemented RPMI (GibcoBRL (Gaithersburg, Md.) as previously described (14). The CHO-K1 cell line (ATCC) and the CD23⁺ CHO-K1 cell line, a previously established transfected CHO cell line expressing murine CD23 (13), were maintained as previously described (13). The murine mast cell line C57 (a generous gift from Stephen Galli, Boston, Mass.) was maintained in IMDM, supplemented with L-glutamine, Pen/Strep, 10% FBS, and non-essential amino acids (GibcoBRL).

Mouse IgE from H1-DNP-ε-26(15) was purified from ascites as described elsewhere (16) and monoclonal anti-CD23 (B3B4(6) or 2G8(7)) were purified from rat ascites. B3B4 and 2G8 are both rat anti-mouse CD23 antibodies that interact at a site similar, but not identical to the side on CD23 that binds IgE. Rabbit B is a polyclonal anti-CD23 antibody purified from rabbit serum as previously described (7). M15, a mouse IgG$_1$ anti-leucine zipper, was obtained from Immunex (Seattle, Wash.)(17). B1E3 is a monoclonal rat anti-mouse IgE antibody that was purified from rat ascites (18). Antibodies were coupled to Affigel-10 from BioRad Laboratories, Inc (Richmond, Calif.) at a concentration of 1 mg/ml. Protein A/Protein G Sepharose was purchased from Pierce (Rockford, Ill.).

Preparation of Chimeric CD23 Constructs

The EC-CD23 construct was made and expressed in a eukaryotic expression vector as previously described (14). The MBP-Cd23 chimera was composed of the leader sequence and stalk of MBP-C(19) and the lectin domain of CD23. The cDNA fragment encoding the signal sequence and stalk of MBP was generated by PCR using MBP-C in pBSKS (a generous gift of Dr. Kurt Drickamer) with primers that added a 5' Hind III site (CAT/CCGAAGCTTGTGAGGACCATG) (Seq. ID No. 1)and a 3' Hinc III site (CTTCTTTCAACATTTTCACT) (Seq. ID No.

2). The cDNA fragment for the lectin head of CD23 (a.a. 189 to the end) was generated by PCR using the cDNA for murine CD23 in pCDM8 and the following primers which added a 5' Sma I site (GATCCCGGGATTTCAAAGGGAACT) (Seq. ID No. 3) and a 3' Not I site (ACAAAGATCCTCTAGAGTCGCGGC) (Seq. ID No. 4). The MBP and CD23 cDNAs were ligated simultanewus into pC-DNA-1-amp that had been digested with Hind III and Not I. Sequence analysis was performed to confirm that the junction between MBP and CD23 was in frame.

The chimeric CD23 protein composed of the cytoplasmic domain, transmembrane domain and stalk of CD72 and the lectin head of CD23 was made using a similar PCR-based strategy. The cDNA of CD72 was generated by PCR using CD72 in pBSKS with a 5' primer (TCACACAGGAAACAGCTATGAC) (Seq. ID No. 5) and a 3' primer which added a Hpa I site (AATGTTAACGGAGGACAAGCGCCTCAG) (Seq. ID No. 6) and was cloned directly into the PCR cloning vector PCRII (Invitrogen). CD72 in pCRII was digested with Hind III and Hpa I and ligated in frame to the lectin head of CD23 (same fragment as used with MBP) in pBSKS that has been digested with the same enzymes. The CD72-CD23 cDNA was moved from pBSKS into the eukaryotic expression vector pC-DNA-1-amp via Hind III and Not I digestion. Sequence analysis performed by the Nucleic Acid Core Laboratory (VCU, Richmond, Va.) detected a frame-shift mutation that was corrected using the Chameleon Site-Directed Mutagenesis Kit (Stratagene). Further sequencing analysis confirmed that the final product was free of any mutations. The CD72-CD23 neck chimera was made using the same CD72 cDNA as created for the above chimera, cloned in frame to the "neck" and lectin head domain of CD23. The "neck" domain of CD23 contains a.a. 157 through 188. PCR was used to generate the CD23 neck cDNA using the following 5' primer which added a Hpa I site (GGCGTTAACGAGAAGCGCACA) (Seq. ID No. 7) and 3' primer which added a 3' Not I site (GAATAGTCGACTCTAGATGCATGCTC) (Seq. ID No. 8). The CD72 and CD23 neck cDNAs were cloned in frome after digestion with Hind III and Not I and ligated into the eukaryotic expression vector pCDNA-3 (Invitrogen). Final sequence analysis determined that the final product was free of PCR-induced mutations.

Human-mouse CD23 was made as previously described (13). To analyze this chimeras ability to bind rIgE, the cDNA was moved from pCDM8 into the high expression vector pEF-BOX (20). The cDNA of human-mouse CD23 was cloned into pEF-BOS after digestion with Xba I and clones containing the insert in the correct orientation were used in the analysis.

Preparation of Protease Resistant and Isoleucine Zipper Chimeric Constructs

The first cleavage site of CD23 was mutated from an asparagine to an alanine to create Cleavage Mutant 1 (C1M0 using the mega primer PCR-based mutational strategy (21) with the following primers: 5' (ATCGATATGGAAGAAAATGAATAC) (Seq. ID No. 9) and 3' (CTTGCAAGGCTTGTGACATCT) (Seq. ID No. 10). The cDNA product was used in a subsequent PCR reaction as the 5' primer along with a 3' primer (GTCGACTCAGGGTTCACTTTTT) (Seq. ID No. 11) to generate the C1M cDNA which was directly cloned into pCRII. The cDNA was further modified by PCR to create a 5' BamHI site (CGGGATCCATGGAAGAAAATCAAT) (Seq. ID No. 12) and a 3' EcoRI site (GGAATTCTCAGGGTTCACTTTTTGG) (Seq. ID No. 13) allowing direct cloning into the PCR cloning vector pCRII. Subsequent digestion with EcoRI allowed the cDNA to be cloned into pC-DNA-3 (Invitrogen). Sequence analysis determined that the final product was free of PCR-induced mutations. A stable C1M cell line was created by electroporating CHO-K1 cells with C1M in pC-DNA-3 and using Neomycin to select for positive clones. Electroporation was performed as previously described (22). CD23 surface expression was monitored by FACS analysis.

The lzEC-C1M construct contained the same sequence of cDNA used to create the full-sized soluble CD23 ((EC-CD23 (14)) with the following exceptions: 1) the first cleavage site in CD23 was mutated from an asparagine to an alanine and 2) a modified leucine zipper motif was added to the amino terminus. The cDNA encoding the leader peptide from the FceFI -leader (23) was used as with EC-CD23 (14) utilizing the Hpa I site to clone the cDNAs together in frame. The sequence for the modified leucine zipper, lz, was graciously provided by Dr. Melanie Spriggs at Immunex (Seattle, Wash.) (24). The cDNA of the lz was synthesized such that both Hind III and Hpa I sites were present at the 5' end and a EcoRI site was present at the 3' end allowing for in frame cloning with the -leader and EC-C1M. The lz was created by annealing four oligonucleotides together to give the correct amino acid sequence. EC-C1M was generated by PCR using C1M in pCDNA-3 as the template along with primers that added a 5' EcoRI site (CTGCTGAATTCTTGGCACTGGGA) (Seq. ID No. 14) and a 3' Not I site (TGATGGATATGCGGCCGCTTCTCA) (Seq. ID No. 15). After restriction enzyme digestions, the three cDNA fragments were cloned together in frame into pCDNA-1-amp (Invitrogen). Sequencing analysis performed by the Nucleic Acid Core Laboratory (VCU, Richmond, Va.) detected several mutations that were corrected using the Quickchange Mutagenesis Kit (Stratagene). Further sequencing analysis confirmed that the final cDNA was correct. Finally, the complete lzEC-C1M cDNA was cloned into the high expression vector pCR4 (a generous gift from Dr. Greg Buck, VCU, Richmond, Va.), a plasmid derived from pEF-BOS (20) which was constructed to include additional cloning sites, including Sal I and Cla I. The cDNA was cloned into pCR4 using PCR to add a 5' Cla I site (TACGACTCAATCGATGGAGACCCAAGCTTG) (Seq. ID No. 16) and a 3' Sal I site (AGGTTCCTTCACGTCGACCCTCTAGCATT) (Seq. ID. No. 17) to the end of the cDNA.

Preparation of Transient Transfected Cells

COS cells were collected in log phase growth and electroporation was performed as previously described (13). Protein expression was analyzed using [$^{35}$S] -metabolic labeling ([$^{35}$S]-translabel protein labeling mix (NEN/Dupont) of either transiently transfected COS, permanently transfected C1M in CHO-K1, or CD23$^+$ in CHO-K1 as previously described (14). Cells were labeled two days after transient transfection, or one day after seeding a medium flask with 5×10$^6$ cells of permanently transfected CHO cells. Media contained 0.4 mM calcium nitrate, sufficient to allow AgE binding to occur (25). To control for differences in either C1M or native CD23 expression, untransfected CHO cells were added to the CD23$^+$ cells prior to [$^{35}$S]-labeling to give similar total CD23 levels. Supernatants containing [$^{35}$S]-labeled protein were subjected to affinity chromatography as previously described (14). Alternatively, supernatant from transfected cells was isolated and the concentration of sCD23, EC-CD23, or lzEC-C1M was determined using a sCD23 ELISA.

Soluble CD23 ELISA

The concentration of sCD23, EC-CD23 or lzEC-C1M present in supernatant of transfected cells was determined using an assay similar to the IgE ELISA previously described (7), instead using the following antibodies. Plates were coated with 20 μg/ml of 2G8 and 5 μg/ml of Rabbit B was added following incubation with unknown samples. EC-CD23 was prepared in house and used as standard. A 1:500 dilution of goat-anti-rabbit HRP (Southern Biotechnologies Associates, Inc., Birmingham, Ala.) was used as the detection antibody followed by the addition of TMB One Step Substrate (Dako Corp., Carpintera, Calif.). The reaction was stopped with 0.18M $H_2SO_4$ and read at wavelength 450 nm. Standard curves were run and four parameter analysis was performed using Molecular Devices software. All ELISA determinants were performed with a duplicate series of dilutions. Dilution values that fell in the linear portion of the curve were used for analysis.

Binding Analysis

The capacity of membrane-bound chimeric proteins to bind [$^{125}$I]-labeled B3B4 or mIgE was performed to detect expression of the lectin head and to test for the ability to interact with IgE. Scatchard analysis was performed as previously described (13). Analysis of the CD72-CD23 chimera was performed by adding two million cells with 100-fold excess of unlabeled IgE or B3B4 and incubated on ice for 10 minutes. Subsequently, 10 μg/ml [$^{125}$I]-IgE or 2 μg/ml [$^{125}$I]-B3B4 was added (final volume 0.5 ml) and the incubation was continued for 60 minutes at 4° C. Alternatively, chimeric or recombinant proteins were analyzed for the ability to inhibit [$^{125}$I]-labeled mIgE binding to CD23 or FcϵRI using CD23$^+$ CHO-K1 cells or C57 mast cells (a generous gift of Stephen Galli, Boston, Mass.), respectively. The indicated amounts of inhibitor were added to [$^{125}$I]-labeled mIgE and allowed to incubate on ice for 10 minutes. Two million cells were added and the incubation was continued for 60 minutes at 4° C. With all protocols, cell bound radioactivity was then determined using the phthalate oil cushion procedure (13). Specific binding was determined by subtracting controls that were incubated with 100-fold excess of cold IgE or anti-CD23 (B3B4). Molecules bound per cell were calculated based on the specific activities of the respective proteins.

RESULTS

Replacement of the Stalk of CD23 With Any Stalk Other Than CD23 Abrogates IgE Binding.

In an effort to analyze the structural requirements for high affinity binding to IgE, several different chimeras were made that contained the lectin domain of CD23 (see FIG. 7 for schematic representation of the various domains of CD23) attached to the stalk domain from proteins known to form oligomers. A soluble chimera was made which contained the lectin domain of CD23 and the stalk from MBP-C. MBP-C contains a collagen-like stalk which is known to mediate trimer as well as higher oligomer formation (19). To determine both if MBP-CD23 was being expressed as a monomer or an oligomer and if the protein could bind IgE, COS were transiently transfected with MBP-CD23, labeled with [$^{35}$S]-translabel, and affinity chromatography was used to purify the labeled chimera. As a positive control for protein expression and IgE binding, CHO-K1 cells transfected with EC-CD23 were used.

Figure 1A:
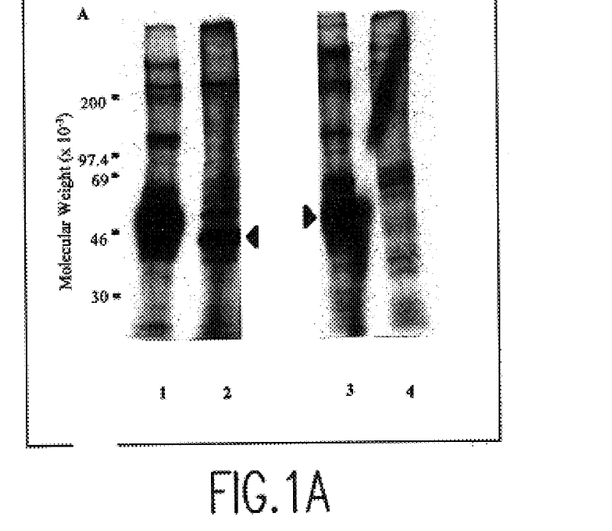
FIGS. 1a–b are electrophoresis gels showing MBP-CD23 is Expressed as a Oligomer, but Cannot bind mIgE The MBP-CD23 chimera was expressed in COS Cells in a transient transfection and labeled overnight with [$^{35}$S]-translabel as described in the Materials and Methods. EC-CD23 transfected cells were labeled and used as a positive control. Supernatants were subjected to affinity chromatography and were isolated by boiling in reduced (A) or non-reduced (B) SDS sample buffer. Samples were run on a 8–18% gradient gel. Both EC-CD23 (lane 1) and MBP-CD23 (lane 2) are recognized by B3B4. EC-CD23 (lane 3) but not MBP-CD23 (lane 4) can bind mIgE. Samples analyzed in non-reduced sample buffer (B) indicates that both EC-CD23 (lane 1) and MBP-CD23 (lane 2) form oligomers, but this does not effect MBP-CD23's ability to bind mIgE (lane 4).
Figure 1B:
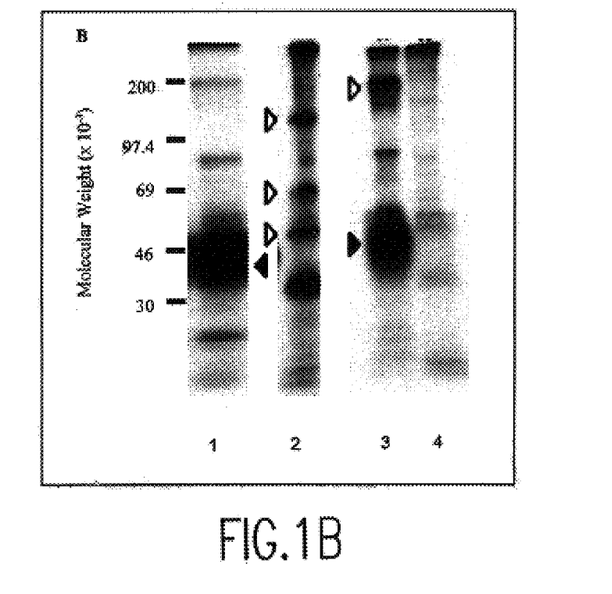

FIGS. 1a and b show that labeled protein analyzed by SDS-PAGE run in (A) reduced or (B) non-reduced sample buffer. In both gels it is evident that the MBP-CD23 cannot bind IgE (lane 4) even though it is recognized by B3B4 (lane 3); neither protein bound to a non-specific affinity column. This lack of affinity for IgE is not due to lack of oligomerization, as shown by the presence of higher molecular weight forms of MBP-CD23 (lane 2) isolated in non-reducing sample buffer. Note that the stalk of MBP is capable of forming oligomers even in the presence of SDS. These data indicate that while the MBP stalk does cause oligomer formation, oligomerization of the lectin head alone is insufficient to allow for recognition of IgE, at least not by utilizing a collagen-like stalk.

Figure 2:
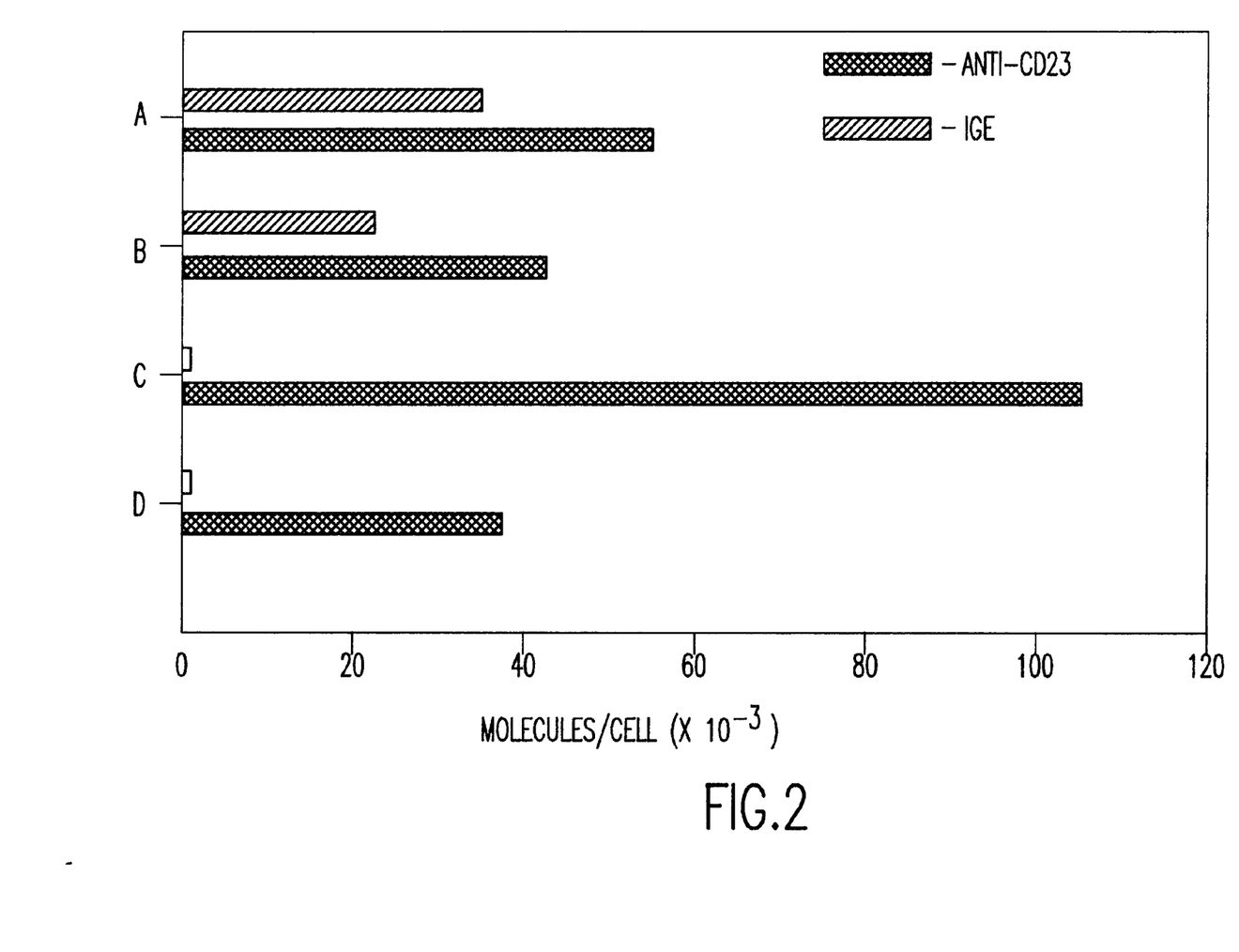
FIG. 2 is a bar graph showing CD72-CD23 can bind B3B4 but cannot bind mIgE The CD72-CD23 chimera was expressed in COS cells in a stable transfection using CHO/DHFR⁻ cells and binding analysis was performed as described in the Materials and Methods to ascertain the chimera's affinity for mIgE. CD23⁺ CHO-K1 (A) or CD23⁺ COS (B) cells were used as positive controls and untransfected cells were used as the negative control to determine non-specific binding. The graphs show that while the B3B4 epitope of CD23 is expressed in two separate clones (clone 10 (C) and clone 3 (D)), the chimera cannot bind mIgE. IgE binding to CD23 is approximately half that seen with anti-CD23 in samples where binding occurs.

Two membrane-bound chimeras were made which contained the stalk of CD72. CD72 is a type II integral membrane protein and a member of the C-type animal lectin family (26). Sequence analysis and homology pattern search indicate that the stalks of both CD23 and CD72 contains the same heptad periodicity indicative on an -helical coiled-coil structure (27;28). Thus, a membrane bound chimera was made containing the cytoplasmic, transmembrane and stalk domains of CD72 and the lectin head of CD23. Both transient and stable transfections determined that CD72-CD23 could not bind mIgE with a measureable affinity even though the epitope recognized by B3B4 was present (See FIG. 2). Since CD72-CD23 was unable to bind mIgE even though the stalk of CD72 is highly homologous to CD23, it was argued that not enough of the lectin domain of CD23 had been included to allow for both high and low affinity binding. Surfactant-D, a member of the collectin family, has been shown to contain a 35 a.a. "neck" domain which mediated the formation of an helical coiled-coil region (29). Studies indicate that the neck and lectin domain of surfactant D alone were capable of not only trimerizing, but also retained the ability to bind its ligand in a multivalent manner (29). Since both CD72 and CD23 are members of the same family as surfactant-D, and the carboxy portion of the stalk of CD23 contains a.a. that are conducive to forming a "neck" region, it was thought that a "neck" domain may be responsible for orienting the lectin heads such that it could properly interact with IgE. To test this, a second chimera was made that was similar to CD72-CD23, but in addition contained the "neck" domain of CD23 (see FIG. 7). The CD72-CD23 neck chimera contained the same domain from CD72 attached to the "neck" and lectin domain of CD23. The putative "neck" domain of CD23 contained amino acids 158 through 188. In contrast to the reports on surfactant-D (29), the addition of the neck had no effect on mediating a interaction with mIgE. Expression analysis of the chimera using a transient transfection in COS or a stable expression in CHO-K1 determined that the chimera could not bind IgE, even though the B3B4 epitope was present. These data indicate that the absence or presence of the neck domain used with the homologous stalk of CD72 is not sufficient to allow for the lectin domain of CD23 to bind IgE.

Analysis of Human-mouse CD23 Chimera

The data from the above chimeras indicated that the stalk of CD23 may not only be important for oligomerization, but may also be important in regulating the interaction with IgE. An human-mouse CD23 chimera previously made by this lab was found to bind mIgE (13) with a dual affinity. Murine CD23, as expressed on the cell surface can interact with both mIgE and rat IgE (22;22). Scatchard analysis was performed to investigate if this chimera could also bind rat IgE. The data from initial experiments indicated that human-mouse CD23 could not bind rat IgE. To determine if low affinity binding was occurring, the cDNA for the chimera was moved into the high expression vector pEF-BOS. The results from the Scatchard analysis determined that while the chimera could bind mIgE with both a high and low affinity (13), it could only bind rat IgE with a low affinity (see FIG. 3).

These data indicate that while the human stalk of CD23 does mediate oligomerization as determined by the chimeras ability to bind mouse IgE with a dual affinity, it does not enable to chimera to interact with rat IgE indicating that there may be another site(s) present that is responsible for this interaction.

C1M is not as Sensitive to Proteolytic Degradation

Figure 4:
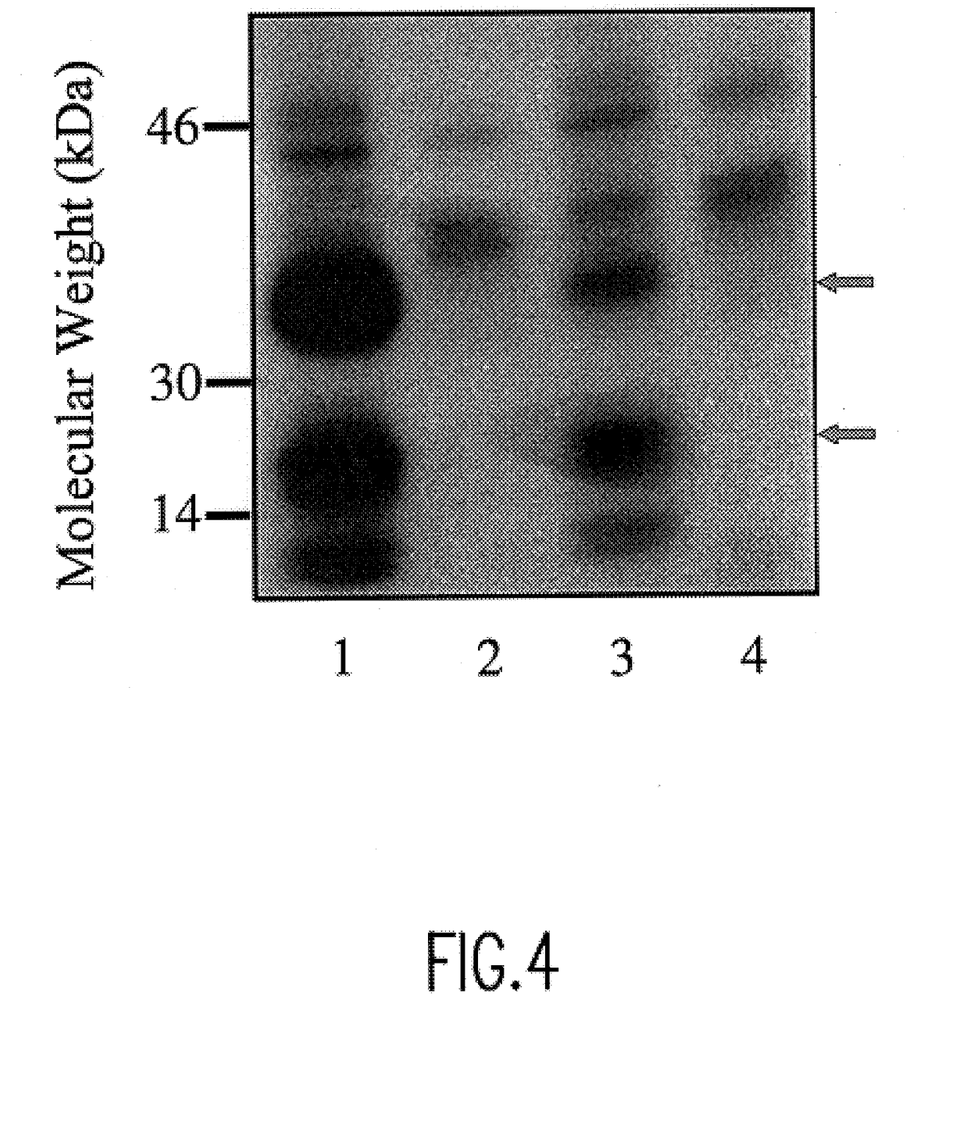
FIG. 4 is an electrophoresis gel which shows that C1M has a reduced amount of cleavage compared to CD23 CD23 or C1M transfected CHO-K1 cells were labeled with [$^{35}$S]-translabel and supernatants were subjected to affinity chromatography as described in the Materials and Methods. Bound protein was boiled in reduced sample buffer to remove the protein from the affinity matrix and analyzed by SDS-PAGE. Neither CD23 (lane 2) or C1M (lane 4) bound to a non-specific affinity matrix (B1E3). Both CD23 (lane 1) and C1M (lane 3) bound the anti-CD23 (B3B4) affigel, but note that the amount of material (sCD23) released into the supernatant is subtantially less (position is indicated by the arrows at the right; arrows indicate 38 kDa and 28 kDa forms of sCD23, respectively) in the supernatant isolated from C1M transfected cells compared to CD23 transfected cells.

Work on EC-CD23 combined with the information gained from the above mentioned chimeras suggested that for high affinity binding to IgE to occur, the entire stalk of CD23 must be present. At the same time, the stalk of CD23 is extremely susceptible to proteolytic degradation from the cell surface (30). In an attempt to create a more stable form of CD23, a cleavage resistant mutant (C1M) was created by mutating the first cleavage site from an asparagine to an alanine in the hopes that this mutation would render the stalk more resistant to proteolytic degradation. Release of sCD23 from C1M transfected cells was analyzed by [$^{35}$S]-metabolically labeling CD23 or C1M transfected CHO-K1 cells, subjecting supernatants to affinity chromatography and analyzing by SDS-PAGB. Note that this analysis assumes the same specific activity for C1M and CD23 from their respective transfected cell population. In order to control for this as much as possible, the total level of receptor expression was adjusted to the same level by adding untransfected CHO cell prior to [$^{35}$S]-labeling. This gave a similar CD23 level in both populations as judged by FACS analysis. The observation that background binding (lanes 2 and 4) were similar further suggests that the level of labeling between C1M and CD23 was comparable. The experiment shown in FIG. 4 is representative of three of similar design. In all cases there was a drastic reduction in the release of sCD23 from C1M transfected cells (lane 3) compared to CD23 transfected cells (lane 1). These data indicate that mutating the first cleavage site does not result in a more stable protein.

Figure 5:
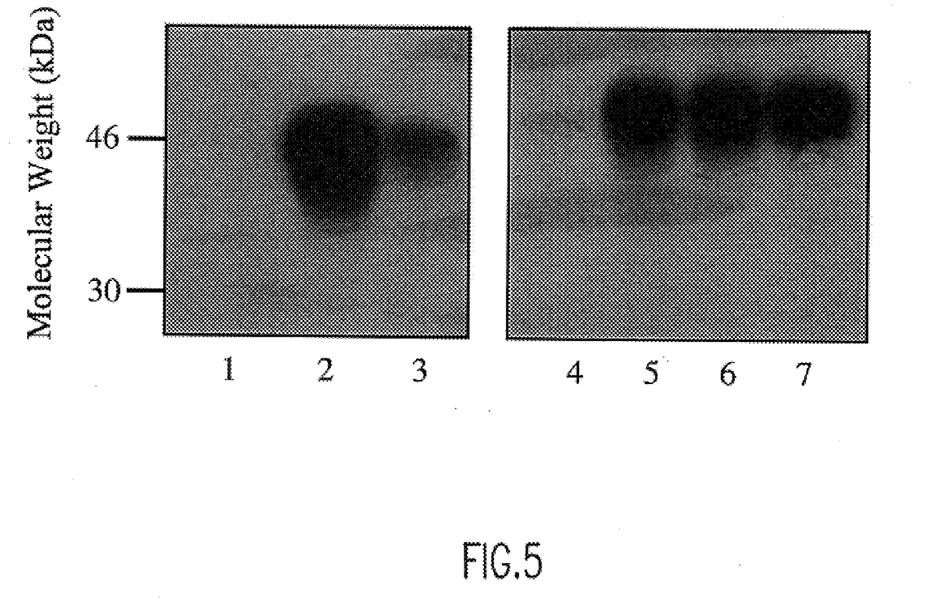
FIG. 5 is an electrophoresis gel showing lzEC-C1M can bind mIgE with a higher affinity than EC-CD23. EC-CD23 or lzEC-C1M transfected COS were labeled with [$^{35}$S]-translabel and supernatants were subjected to affinity chromatography as described in the Materials and Methods. Bound protein was eluted from the affinity matrix by boiling in reduced sample buffer and analyzed by SDS-PAGE. Neither EC-CD23 (lane 1) nor lzEC-C1M (lane 4) bound to a non-specific affinity matrix (B1E3). Both EC-CD23 (lane 2) and lzEC-C1M (lane 5) bound the anti-CD23 (B3B4) affigel, but the lzEC-C1M interacted with the mIgE (lane 6) affigel with a much higher affinity than the EC-CD23 (lane 3). The leucine zipper portion of the protein was expressed in the chimera as the addition of M15, a anti-leucine zipper antibody, to the supernatant from lzEC-C1M transfected COS allowed for the chimera to be immunoprecipitated by a Protein A/Protein G affigel (lane 7).

Addition of a stabilizing motif to the amino terminus of CD23 results in high affinity binding to mIgE The creation of C1M resulted in the formation of a more stable form of CD23. This mutation was combined with the addition of a protein motif to the amino terminus of EC-CD23 that would allow for more stable trimer formation that normally seen with EC-CD23. Fanslow, et al. (24) reported the use of a modified isoleucine zipper for the preparation of a soluble trimeric CD40L. The use of this motif is based on X-ray crystallography which demonstrated that replacing leucines with isoleucines results in the creation of stable trimers (31). Thus, this approach was used for EC-CD23. The modified isoleucine zipper was fused to the amino terminus of EC-CD23 (including the C1M mutation) to the force the protein to form a stable trimer (see FIG. 7 for schematic representation of lzEC-C1M). The cDNA of CD-C1M CD23 was cloned in frame to the isoleucine zipper, resulting in the creation of lzEC-C1M. Optimal expression of the chimera was obtained using lzEC-C1M cloned into the high expression vector pCr4. COS cells transiently transfected with lzEC-C1M or EC-CD23 were metabolically labeled with [35S]-translabel. The supernatants were subjected to affinity chromatography and analyzed by SDS-PAGE. FIG. 5 shows the data from these experiments which indicate that the lzEC-C1M can bind mIgE (lane 6) just as well as it is bound by B3B4 (lane 5). FIG. 5 (lane 7) also shows that the isoleucine zipper motif is expressed since the protein can be immunoprecipitated with a Protein A/Protein G affinity matrix that has been incubated with a anti-leucine zipper antibody, M15, and supernatants from the lzEC-C1M transfected cells. The lzEC-C1M is also capable of binding mIgE better than EC-CD23 as can be seen by comparing lane 6, the lzEC-C1M, to lane 3, EC-CD23. Data is representative of two experiments.

IZEC-C1M Can Inhibit Binding of IgE to Both CD23 and Fc∈RI

Figure 6A:
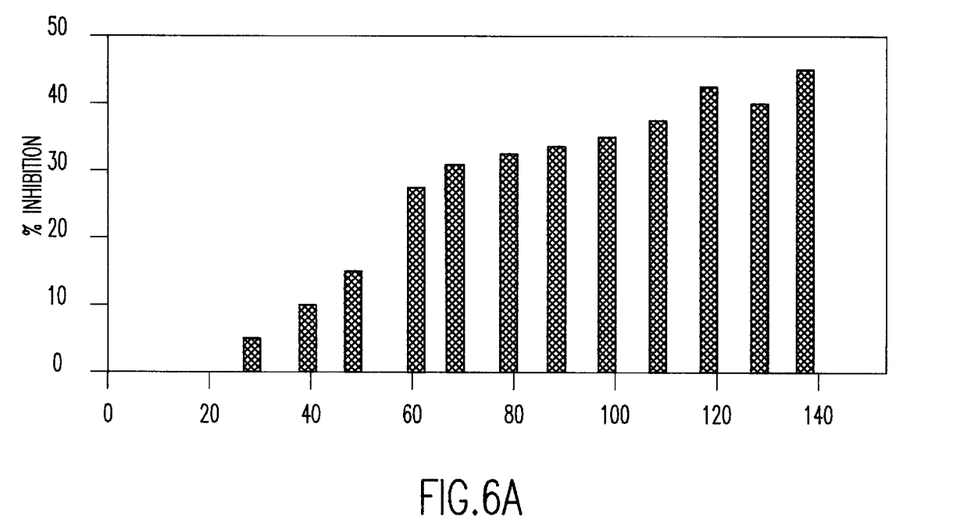
FIGS. 6a and 6b are bar graphs showing lzEC-C1M inhibits [$^{125}$I]-mIgE binding to CD23⁺ CHO-K1 cells and C57 mast cells in a dose dependent manner. Increasing volumes of supernatant from lzEC-C1M transfected COS were added to CD23⁺ CHO-K1 cells (A) or C57 mast cells (B) in a binding assay as explained in the Materials and Methods. At the highest concentration of lzEC-C1M, 138 ng, there was close to a 50% inhibition of [$^{125}$I]-mIgE binding to CD23 (A) and almost a 80% inhibition of [$^{125}$I]-mIgE binding to the high affinity receptor FcεRI (B).
Figure 6B:
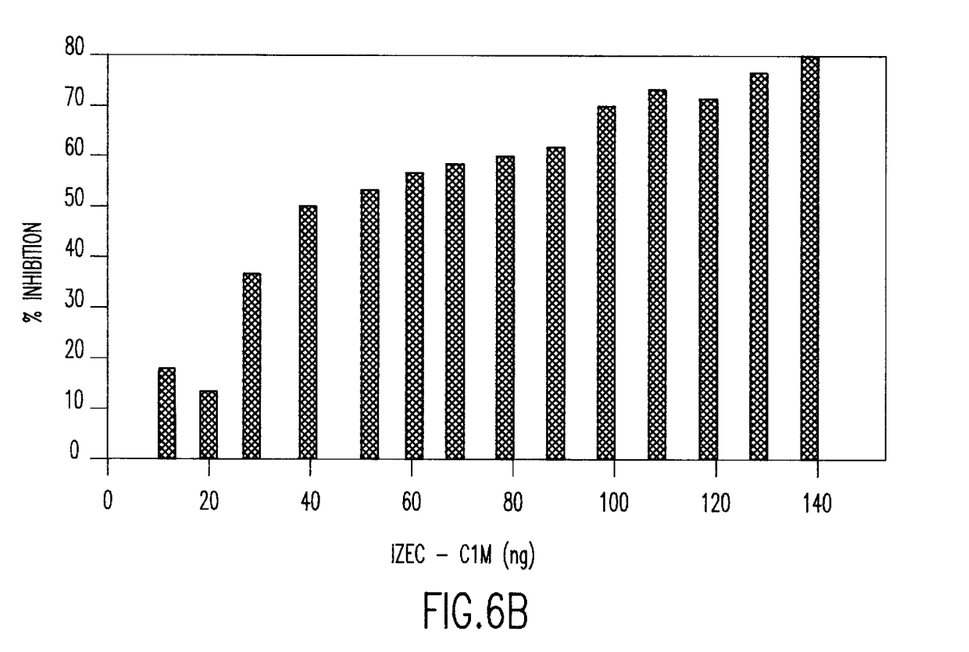

The relative affinity of the lzEC-C1M for IgE appears to be much higher than that of EC-CD23 and this result is most likely due the stable trimeric confirmation of the chimera. Due to the increased ability to interact with IgE, the lzEC-C1M was analyzed for its ability to inhibit migE binding to CD23 or Fc∈RI. Binding analysis was performed using CD23$^+$ CHO-K1 or C57 mast cells, adding a constant concentration of [$^{125}$I]-labeled mIgE and an increasing concentration of the lzEC-C1M. Percent inhibition was determined by using the binding of [$^{125}$I]-mIgE to the cells that were incubated with media from mock transfected COS. FIG. 6a shows that 138 ng of lzEC-C1M can inhibit by almost 50% the binding of mIgE to CD23$^+$ CHO-K1 cells. In addition, the same concentration of the lzEC-C1M can inhibit mIgE binding to the Fc∈RI on mast cells by 80%. The same experiments were performed with EC-CD23 isolated from transiently transfected COS cells and there was no more that a 10% inhibition of mIgE binding to CD23$^+$ cells or to mast cells. To ensure that the mast cell line used was not aberrantly expressing the low affinity receptor for IgE, the cells were analyzed by FACscan for their ability to bind mIgE as well as looking at CD23 expression. While the cells could bind mIgE, there was no CD23 expressed on these mast cells.

DISCUSSION

Previous work on CD23 from several different laboratories has determined that CD23 must be an oligomer in order to bind IgE with a high affinity (13), (32), (27); this includes early data indicating that CD23 can self-associate to form a trimer or tetramer as indicated by its molecular weight following treatment with chemical cross-linking reagents (33) and that the stalk region of CD23 (a.a. 55 to 157) is important in this oligomerization. Several chimeric proteins were previously useful in investigating various aspects of CD23 structure function. This data is summarized in Dierks, et al. (13) and Bartlett, et al. (14) and allowed the conclusion that the cytoplasmic and transmembrane domains of CD23 have no role in IgE binding and function only to anchor the protein on the cell surface. On the other hand, the stalk of CD23 is required to bind IgE either because it is needed to mediate oligomerization or because it can directly interact with IgE. This study extended this aspect of the stalk requirement through the analysis of several additional unique CD23 chimeras as well as further analysis of the human-mouse CD23 chimera.

Figure 3A:
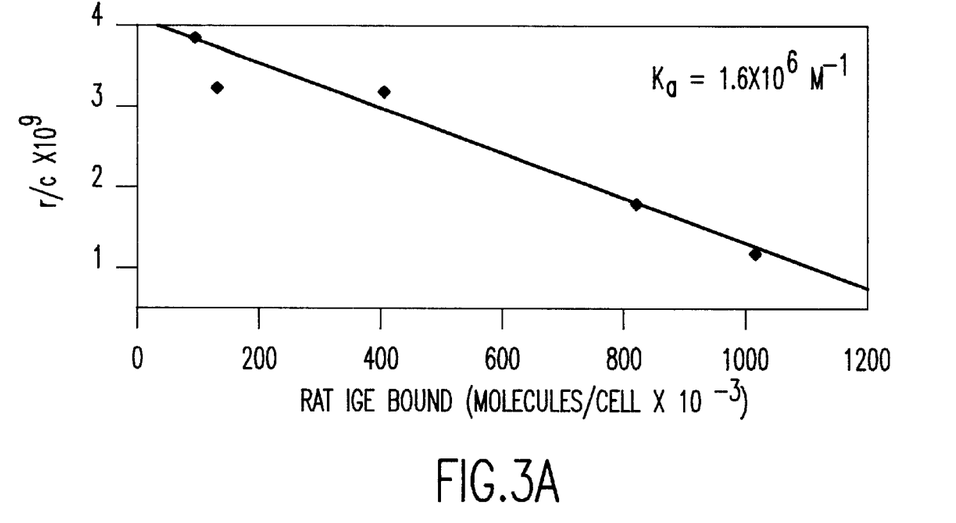
FIG. 3 is a two panel line graph showing Human-Mouse CD23 can only bind rIgE with a low affinity The Human-Mouse CD23 chimera in pEF-BOS was expressed in COS cells in a transient transfection and binding analysis was performed as described in the Materials and Methods to ascertain the chimera's affinity for rat IgE. The data was analyzed by Scatchard analysis and graphs (representative of two separate experiments) show that the chimera can only bind rat IgE with a single low affinity; the association constants for low affinity binding is shown in the upper right hand corner.
Figure 3B:
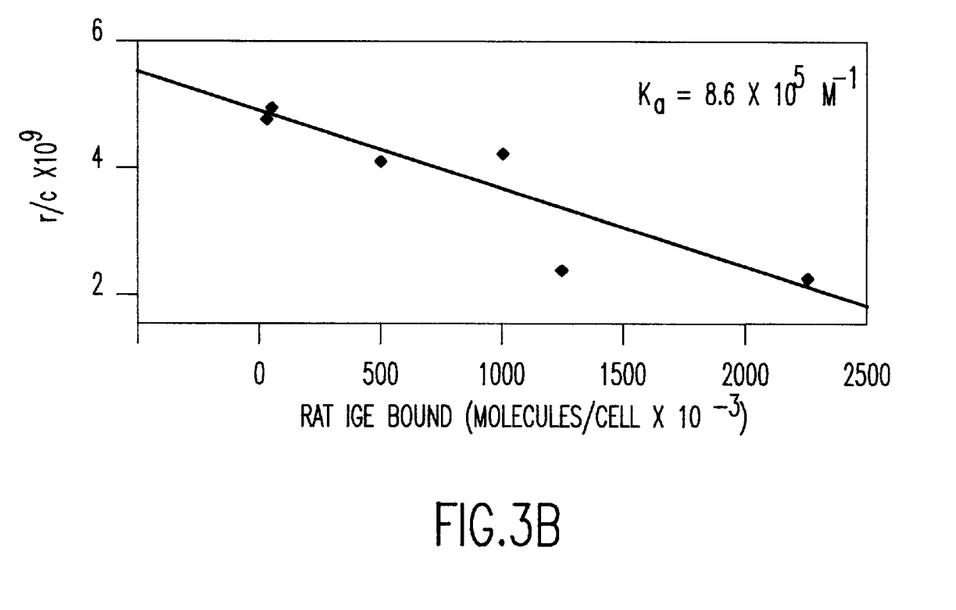

The latter chimera was previously reported to interact with IgE with dual affinity (13). Studies described above in this patent application examined the ability of human-mouse CD23 to bind rIgE (FIG. 3). Using a high protein expression system, the human-mouse CD23 could not bind rIgE even though murine CD23 normally interacts with both rat and mouse IgE (22). This indicates that there are site(s) within the stalk that bind IgE and there is enough homology between the stalk of human and mouse CD23 that binding to mIgE was unaffected, but the homology between the region required to bind rIgE was not as conserved. Regardless, this disparity points to the fact that the role of the stalk may not be as simple as to only mediate oligomerization.

Several new chimeras were made in the attempt to create a stable oligomeric form of CD23 that could bind IgE with an affinity higher than EC-CD23. The initial chimeras utilized the lectin head of CD23 combined with stalks from proteins known to form oligomers. Interestingly, neither the stalk from MBP, a protein known to form trimers and hexamers via its collagen-like stalk (19), nor the stalk of CD72, a protein homologous to CD23 with respect to the predicted coiled-coil structure of the stalk, enabled the respective chimeras (FIGS. 1 and 2) to bind IgE, analogous to the results seen with the Ly-49-CD23 chimera composed of the stalk of Ly-49 (14). Also, the addition of the "neck" domain, by analogy with surfactant-D (29), did not improve the binding capacity of the CD72-CD23 chimera. Studies performed with only the neck and lectin domain of surfactant-D was shown capable not only of trimerizing, but also retained that ability to bind its ligand in a multivalent manner (29). Since both CD72 and CD23 are members of the same family as surfactant-D, and the carboxy portion of the stalk of CD23 contains amino acids that are conducive to forming a "neck" region, it was thought that a "neck" domain may be responsible for orienting the lectin head such that it could properly interact with mIgE. In all cases, confirmation of in frame chimeric production was monitored via the interaction with anti-CD23. These data combined with data from the previously mentioned chimeras imply that replacing the stalk of CD23 with any other stalk completely abrogates the capacity to bind IgE.

EC-CD23 was previously created in order to investigate the role that the stalk plays in mediating a high affinity interaction with IgE (14). A problem found with the full-sized extracellular EC-CD23 was the stability of the molecule. The creation of sCD23 naturally occurs by proteolytic cleavage within the stalk resulting in the release of a 38 kDa fragment, with subsequent cleavage forming 35 kDa, 28 kDa, and 25 kDa species (14) (6) (34). Murine sCD23 can inhibit binding of IgE to CD23$^+$ cells at high concentrations (14), but can not bind IgE with an affinity comparable to that seen with the membrane form. The C1M mutant was made in an attempt to create a form of CD23 that was not subject to this same degree of proteolytic degradation. The mutation of the first cleavage site from an asparagine to an alanine did result in a form of CD23 that released decreased quantities of sCD23 (see FIG. 4). While this data assumes similar specific activities for the [$^{35}$S]-labeling, adjustment of CD23 levels at initiation of labeling combined with the strong decrease in sCD23 seen indicate that this mutation had the desired effect. This mutation was utilized in the creation of a soluble chimeric CD23 which would allow further investigation of the role that a stable stalk plays in mediating the interaction with IgE.

The chimeric data combined with the data from EC-CD23 demonstrated that the stalk of CD23 was more important in promoting both trimerization and IgE binding than was previously thought. Previous work with EC-CD23 determined that the addition of the entire stalk did allow for a higher affinity with IgE compared to sCD23, however, the affinity is still a log lower than the affinity seen with CD23. The most feasible explanation for this result is that the trimeric form of EC-CD23 was not sufficiently stabilized resulting in disassociation of the trimer to that of a monomer. If a protein motif could be added to the amino terminal portion of EC-CD23 stabilizing the trimer confirmation in the same manner that the membrane stabilizes CD23 on the cell surface, it was anticipated that such a recombinant protein would bing IgE with an comparable affinity to membrane CD23. The lzEC-C1M made to test this hypothesis contains a modified isoleucine motif that has been shown to form stable trimers (31). As mentioned earlier, the stalk contained a mutation to the first cleavage site resulting in a protein that was not subject to the same degree of proteolytic degradation normally seen with CD23. The resulting chimera's capacity to bind IgE was clearly superior to EC-CD23 (FIG. 5). The increased binding suggests that the capacity to interact with IgE is at least as effective as native membrane CD23. Thus, these data indicate that the inability of sCD23 to bind IgE with a significant affinity results from its inability to form a stable trimer due to the lack of the amino portion of the stalk combined with the loss of the membrane to provide a surface to force oligomerization.

The increased capacity to interact with IgE is dramatically emphasized in that the lzEC-C1M exhibited an excellent capability to block IgE binding to the Fc∈RI. In early work on sCD23, Kishimoto, et al. (35) found that a 10,000 to 100,000-fold excess of sCD23 was required to inhibit IgE binding to the Fc∈RI. The addition of similar concentrations of EC-CD23 expressed in COS resulted in a minimal inhibition of IgE binding to Fc∈RI and to CD23$^+$ cells. In fact, greater than a 50-fold excess of EC-CD23 (expressed in E. coli) was required to see a 50% inhibition, or 100-fold excess for 100% inhibition, of binding to the high affinity receptor. The results with lzEC-C1M indicate that when high affinity binding to IgE is present, only slight excess of this sCD23 chimera would be necessary to effectively block the interaction between IgE and Fc∈RI.

Figure 7:
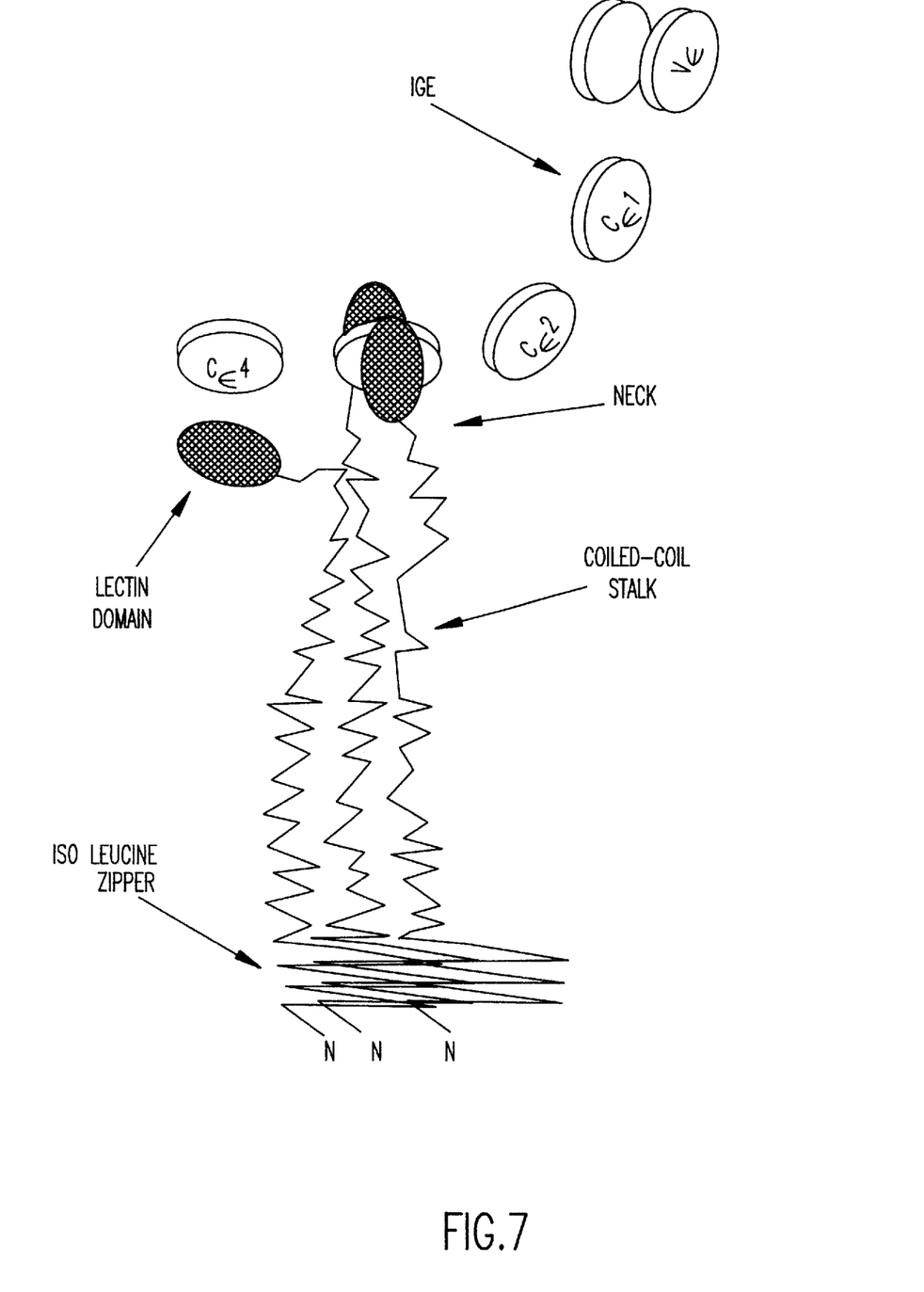

The ability lzEC-C1M to inhibit mIgE binding to Fc∈RI argues that what has been termed affinity should really be termed avidity since the stabilization of the extracellular domain of CD23 allowed for a stronger interaction with IgE. The affinity between two proteins is determine by the strength of binding, while the avidity is dependent on a combination of binding sites (36). In other words, both EC-CD23 and lzEC-C1M may have the same affinity, but the presence of the isoleucine zipper results in the creation of a stable trimer allowing the avidity between IgE and the lzEC-C1M to be higher than that of EC-CD23 because more than one lectin head would be capable of binding to IgE. FIG. 7 shows a schematic representation of how the leucine zipper stabilized EC-C1M by forcing it to form a stable trimeric structure.

The ability of lzEC-C1M to form higher oligomers combined with the fact that CD23 is multivalent may also explain why there is only a 50% inhibition of mIgE binding to CD23$^+$ cells. Lee and Conrad (37) demonstrated the multivalency of CD23 in studies demonstrating the interaction of more than one IgE molecule by a single CD23 molecule. Therefore, any inhibition mediated by CD-CD2 would be masked by the ability of lzEC-C1M to oligomerize with CD23 expressed on the cell surface. If this was occurring, mIgE would be retained on the cell surface even though it was bound to the lzEC-C1M. This will be directly tested once larger quantities of lzEC-C1M are available.

The implications for this protein are important in respect to a potential role as a therapeutic agent for use with IgE mediated disease. Therapies directed against preventing allergy either by inhibiting the protease responsible for cleaving CD23 (38) or through the use of a humanized anti-IgE (39–41) are presently under investigation. Both in vitro data using cells over expressing CD23 97) and in vitro data from CD23 transgenic mice (7;8) corroborates that CD23 can be involved in IgE down-regulation. The lzEC-C1M represents an additional alternative for blocking the interaction of IgE with the Fc receptors expressed on mast cells and basophils. Studies in progress will investigate whether this strategy offers advantages over the anti-IgE and protease inhibition strategies mentioned above.

It is expected that the lzEC-C1M can be administered to patients having IgE mediated disorders such as asthma and allergeries by any pharmaceutically acceptable delivery route (e.g., interperetoneal, intravenous, oral, transcutaneous, subcutaneous, intradermal, inhalation, etc.). The chimeric protein may be combined with either solid or liquid carriers (e.g., lactose, saline, oils, alcohols, etc.), and may be used in combination with preservatives (e.g., parabens, BAK, etc.), anti-inflammatory agents, etc. The dose to be administered will depend on a variety of factors including the disorder being treated, amount of IgE binding desired, patient (e.g., age, sex, race, etc.), delivery route, etc.

REFERENCES CITED ABOVE

1. Yukawa, K., H. Kikutani, H. Owaki, K. Yamasaki, A. Yokota, H. Nakamura, E. L. Barsumian, R. R. Hardy, M. Suemura, and T. Kishimoto. 1987. A B cell-specific differentiation antigen CD23, is a receptor for IgE (FcєR) on lymphocytes. *J. Immunol.* 138:2576.
2. Conrad, D. H. 1990. FcєRII/CD23: The low affinity receptor for IgE. *Ann. Rev. Immunol.* 8:623.
3. Maeda, K., G. F. Burton, D. A. Padgett, D. H. Conrad, T. F. Huff, A. Masuda, A. K. Szakal, and J. G. Tew. 1992. Murine Follicular dentritic cells (FDC) and low affinity Fc-receptors for IgE (FcєRII). *J. Immunol.* 148:2340.
4. Conrad, D. H., A. D. Keegan, K. R. Kalli, R. Van-Dusen, M. Rao, and A. D. Levine. 1988. Superinduction of low affinity IgE receptors on murine B lymphocytes by lipolysaccarade and IL-4. *J. Immunol.* 141:1091.
5. Sarfati, M., T. Nutman, C. Fonteyn, and G. Delespesse. 1986. Presence of antigenic determinants common to IgE Fc receptors on human macrophages, T and B lymphocytes and IgE-binding factors. *Immunology* 59:569.
6. Rao, M., W. T. lett, and D. H. Conrad. 1987. Characterization of a monoclonal antibody directed against the murine B lymphocyte receptor for IgE. *J. Immunol.* 1381:1845.
7. Cho, S. W., M. A. Kilmon, E. J. Studer, H. Van der Putten, and D. H. Conrad. 1997. B cell activation and Ig, especially IgE, production is inhibited by high CD23 levels in vivo and in vitro. *Cell. Immunol.* 180:36.
8. Payet, M. E., E. Woodward, M. A. Kilmon, and D. H. Conrad. 1998. CD23 transgenic mice exhibit a defect in humoral responses. *FASEB J.* 12:A1060. (Abstract)
9. Yu, P., M. Kosco-Vilbois, M. Richards, G. Köhler, M. C. Lamers, and G. Kohler. 1994. Negative feedback regulation of IgE synthesis by murine CD23. *Nature* 369:753.
10. Bonnefoy, J.-Y., J.-F. Gauchat, P. Life, P. Graber, J.-P. Aubry, and S. Lecoanet-Henchoz. 1995. Regulation of IgE synthesis by CD23/CD21 interaction. *Int. Arch. Allergy Immunol.* 107:40.
11. Lecoanet-Henchoz, S., J.-F. Gauchat, J.-P Aubry, P. Graber, P. Life, N. Paul Eugene, B. Ferrua, A. L. Corbi, B. Dugas, C. Plater-Zyberk, and J.-Y Bonnefoy. 1995. CD23 regulates monocyte activation through a novel interaction with the adhesion molecules CD 11b-CD18 and CD 11cCD18. *Immunity* 3:119.
12. Lecoanet-Henchoz, S., C. Plater-Zyberk, P. Graber, D. Gretener, J. P. Aubry, D. H. Conrad, and J. Y. Bonnefoy. 1997. Mouse CD23 regulates monocyte activation through an interaction with the adhesion molecule CD11b/CD18. *Eur. J. Immunol.* 27:2290.
13. Dierks, S. E., W. C. Bartless, R. L. Edmeades, H. J. Gould, M. Rao, and D. H. Conrad. 1993. The oligomeric nature of the murine FcєRII/CD23: Implications for function. *J. Immunol.* 150:2372.
14. Bartlett, W. C., A. E. Kelly, C. M. Johnson, and D. H. Conrad. 1995. Analysis of murine soluble FcєRII: Sites of cleavage and requirements for dual affinity interaction with IgE. *J. Immunol.* 154:4240.
15. Liu, F.-T., J. W. Bohn, E. L. Ferry, J. Yamamoto, C. A. Molinaro, L. A. Sherman, N. R. Klinman, and D. H. Katz. 1980. Monoclonal dinitrophenol specific murine IgE antibody preparation, isolation and characterization. *J. Immunol.* 124:2728.
16. Isersky, C., A. Kulczycki, Jr., and H. Metzger, 1974. Isolation of IgE from reaginic rat serum. *J. Immunol.* 112:1909.
17. McGrew, J. T., D. Leiske, B. Dell, R. Klinke, D. Krasts, S. F. Wee, N. Abbott, R. Armitage, and K Harrington. 1997. Expression of trimeric CD40 ligand in Pichia pastoris: Use of a rapid method to detect high-level expressing transformants. *Gene* 187:193.
18. Keegan, A. D., C. Fratazzi, B. Shopes, B. Baird, and D. H. Conrad. 1991. Characterization of new rat anti-mouse IgE monoclonals and their use along with chimeric IgE to further define the site that interacts with FcєRII and FCєRI. *Mol. Immunol.* 28:1149.
19. Drickamer, K., M. S. Dordal, and L. Reynolds. 1986. Mannose-binding proteins isolated from rat liver contain carbohydrate-recognition domains linked to collagenous tails. *J. Biol. Chem.* 261:6878.
20. Mizushima, S. and S. Nagata. 1990. PEF-BOS, a powerful mammalian expression vector. *Nucleic. Acids Res.* 18:5322.
21. Barik, S. 1993. Site-Directed Mutagenesis by Double Polymerase Chain Reaction Megaprimer Method. In *Methods in Molecular Biology PCR Protocols: Current Methods and Applications.* B. A. White, ed. Humana Press Inc., Totowa, N.J., p. 277.
22. Bettler, B., H. Hofstetter, M. Rao, W. M. Yokoyama, F. Kilchherr, and D. H. Conrad. 1989. Molecular structure and expression of the murine lymphocyte low affinity receptor for IgE. (FcєRII). *Proc. Natl. Acad. Sci. USA* 86:7566.
23. Shimizu, A., I. Tepler, P. N. Benfey, E. H. Berenstein, R. P. Siraganian, and P. Leder. 1988. Human and rat mast cell high-affinity immunoglobulin E receptors: Characterization of putative -chain products. *Proc. Natl. Acad. Sci. USA* 85:1907.
24. Fanslow, W. C., S. Srinivasan, R. Paxon, M. G. Gibson, M. S. Spriggs, and R. J. Armitage. 1994. Structural characteristics of CD40 ligand that determine biological function. [Review]. *Sem. Immunol.* 6:267.
25. Richards, M. L. and D. H. Katz. 1990. The binding of IgE to murine FcєRII is calcium-dependent but not inhibited by carbohydrate. *J. Immunol.* 144:2638.
26. Von Hoegen, I., C.-L. Hsieh, R. Scharting, U. Francke, and J. R. Parnes. 1991. Identity of human Lyb-2 and CD72 and localization of the gene to chromosome 9. *Eur. J. Immunol.* 21:1425.
27. Beavil, A. J., R. L. Edmeades, H. J. Gould, and B. J. Sutton. 1992. -Helical coiled-coil stalks in the low-affinity receptor for IgE (FcєRII/CD23) and related C-type lectins. *Proc. Natl. Acad. Sci. USA* 89:753.
28. Nakayama, E., I. vonHoegen, and J. Parnes. 1989. Sequence of the Lyb-2 B-cell differentiation antigen defines a gene superfamily of receptors with inverted membrane orientation. *Proc. Natl. Acad. Sci. USA* 86:1352.
29. Wang, J.-Y., U. Kishore, and K. B. Reif. 1995. A recombinant polypeptide, composed of the -helical neck region and the carbohydrate recognition domain of conglutinin, self associates to give a functionally intact homotrimer. *FEBS Lett.* 376:6.

30. Lee, W. T., M. Rao, and D. H. Conrad. 1987. The murine lymphocyte receptor for IgE IV. The mechanism of ligand-specific receptor upregulation on B cells. *J. Immunol.* 139:1191.
31. Harbury, P. B., P. S. Kim, and T. Alper. 1994. Crystal structure of an isoleucine-zipper trimer. *Nature* 371:80.
32. Gould, H., B. Sutton, A. Beavil, R. Edmeades, and D. Martin. 1991. Immunoglobulin E receptors. *Clin. Exp. Allergy* 21 *Suppl.* 1: 138.
33. Lee, W. T. and D. H. Conrad. 1985. The murine lymphocyte receptor for IgE.III. Use of chemical cross-linking reagents to further characterize the B lymphocyte Fc epsilon receptor. *J. Immunol.* 134:518.
34. Delespesse, G., U. Suter, D. Mossalayi, B. Bettler, M. Sarfati, H. Hofstetter, E. Kilcherr, P. Debre, and A. Dalloul. 1991. Expression, structure, and function of the CD23 antigen. *Adv. Immunol.* 49:149.
35. Suemura, M., H. Kikutani, M. Aitani, A. Yamatodani, T. Kuritani, S. Kishimoto, N. Uchibayashi, K. Sugiyama, E.L. Barsumian, and T. Kishimoto. 1989. Suppression of IgE-mediated allergic reactions with recombinant soluble Fc∈RII. *7th Int. Congress Immunol* 19–55. (Abstract)
36. Janeway, C. A. and P. Travers. 1996. *Immunobiology: The Immune System in Health and Disease*. Current Biology Ltd., New York.
37. Lee, W. T. and D. H. Conrad. 1984. The murine lymphocyte receptor for IgE.II. Characterization of the multivalent nature of the B lymphocyte receptor for IgE. *J. Exp. Med.* 159:1790.
38. Christie, G., A. Barton, B. Bolognese, D. R. Buckle, R. M. Cook, M. J. Hansbury, G. P. Harper, L. A. Marshall, M. E. McCord, K. Moulder, P. R. Murdock, S. M. Seal, V. M. Spackman, B. J. Weston, and R. J. Mayer. 1997. IgE secretion is attenuated by an inhibitor of proteolytic processing of CD23 (Fc∈RII). *Eur. J. Immunol.* 27:3228.
39. Saban, R., M. Haak-Frendscho, M. Zine, J. Ridgway, C. Gorman, L. G. Presta, D. Bjorling, M. Saban, and P. Jardieu. 1994. Human FcERI-IgG and humanized anti-IgE monoclonal antibody MaE11 block passive sensitization of human and rhesus monkey lung. *J. Allergy Clin. Immunol.* 94:836.
40. Shields, R. L., W. R. Werther, K. Zioncheck, L. O'Connell, T. Klassen, B. Fendly, L. G. Presta, and P. M. Jardieu. 1995. Anti-IgE monoclonal antibodies that inhibit allergen-specific histamine release. *Int. Arch. Allergy Immunol.* 107:412.
41. Saban, R., M. Haak-Frendscho, M. Zine, L. G. Presta, D. E. Bjorling and P. Jardieu. 1997. Human anit-IgE monoclonal antibody blocks passive sensitization of human and rhesus monkey bladder. *J. Urol.* 157:689.

While the invention has been described in terms of its preferred embodiments, the invention can be practiced with modification and variation within the spirit and scope of the appended claims.

We claim:

1. The chimeric protein lzEC-C1M, derived from the extracellular region of CD23, with an isoleucine zipper.

* * * * *